United States Patent [19]

Gaillard

[11] 4,404,415

[45] Sep. 13, 1983

[54] PROCESS FOR PRODUCING NONENES OR FOR SIMULTANEOUSLY PRODUCING NONENES AND DODECENES FROM PROPENE

[75] Inventor: Jean Gaillard, Lyons, France

[73] Assignee: Institut Francais du Petrole, Rueil-Malmaison, France

[21] Appl. No.: 370,322

[22] Filed: Apr. 21, 1982

[30] Foreign Application Priority Data

Apr. 21, 1981 [FR] France .............................. 81 08077

[51] Int. Cl.$^3$ ............................................ C07C 2/24
[52] U.S. Cl. ..................................... 585/512; 585/510
[58] Field of Search ................................ 585/512, 510

[56] References Cited

U.S. PATENT DOCUMENTS 3,592,896  7/1971  Cannell ............................. 585/512
4,283,305  8/1981  Chauvin et al. .................... 585/512
4,320,243  3/1982  Chauvin et al. .................... 585/512

Primary Examiner—Curtis R. Davis
Attorney, Agent, or Firm—Millen & White

[57] ABSTRACT

A process is provided for the production of nonenes or of a nonenes/dodecenes mixture, wherein: propylene is introduced into a liquid reaction phase containing a soluble dimerization catalyst, the temperature is 20°–60° C., at least a portion of the resultant hexenes is recycled and the propylene concentration is maintained between 0.05 and 1% by weight.

6 Claims, No Drawings

PROCESS FOR PRODUCING NONENES OR FOR SIMULTANEOUSLY PRODUCING NONENES AND DODECENES FROM PROPENE

The present invention concerns a process for producing nonenes or a mixture of nonenes and dodecenes from propene.

According to a known process, propene is dimerized in liquid phase in the presence of a catalyst formed by reacting a nickel compound with a hydrocarbyl aluminum halide. The resultant product consists mainly of hexenes with a low proportion of higher olefins, chiefly nonenes and dodecenes. A first object of the present invention is to increase the production of higher olefins, mainly nonenes or a mixture of nonenes and dodecenes. These olefins constitute an outstanding starting material for the oxo synthesis, leading to the formation of alcohols including certain esters, for example phthalates or adipates which constitute outstanding plasticizers. Another object of the invention is to modify the structure of the higher olefins with respect to the olefins obtained by the known process.

These results, and other results which will appear from the following disclosure, are obtained by introducing propene into a liquid reaction phase containing a mixture of hexenes and a dimerization catalyst soluble in the hexenes, the amount of propene thus introduced being so controlled as to maintain the propene concentration in the liquid reaction phase in the range from 0.05 to 1% b.w., discharging a portion of the liquid reaction phase, separating nonenes and higher olefins and recycling at least a portion or the totality of the remaining phase of high hexenes content to the reaction zone.

The control of the propene content can be easily effected by chromatographic analysis in gas phase of the reaction mixture.

The operation can be conducted in an autoclave cooled, for example, by a coil. The reaction mixture is, however, preferably circulated in a loop circuit, successively through the reactor and through an external cooling exchanger; in that case the hourly feed rate of the liquid phase is at least 3 liters and for example, from 5 to 50 liters per liter of the reaction space.

The reaction temperature is usually selected between 20° and 60° C., preferably between 35° and 50° C., and the pressure must be sufficient to maintain the olefins in liquid phase.

Examples of dimerization catalysts soluble in hydrocarbons are complexes wherein a metal, preferably nickel, is bound to at least one hydrocarbon group, for example a bis-$\pi$-allyl nickel, a $\pi$-allyl nickel halide or bis-cyclooctadiene nickel associated to a halogenated aluminum compound. Another type of catalyst consists of the complexes formed by admixing at least one nickel compound with at least one alkylaluminum compound and optionally a ligand, for example a phosphine. These catalysts are well-known in the art. A preferred class of catalysts comprises the catalysts obtained by admixing at least one nickel carboxylate (the carboxylate group comprises at least six carbon atoms) with at least one dichloroalkylaluminum compound or alkylaluminum sesquichloride, the Al/Ni atomic ratio being from 2:1 to 50:1.

The catalyst can be used in a proportion of, for example, 0.1 to 20 milligram-atoms of nickel per kilogram of feed charge, i.e. of propylene-hexenes mixture.

Inert diluents can be used, for example, liquid saturated hydrocarbon diluents.

The invention is not limited to the use of a single reaction stage of the above type. From 2 to 6 stages, preferably 2 to 4 states, can be used in serial arrangement, each stage optionally having its own recirculation system.

When operating with several stages, the whole amount of the reactants and of the catalyst can be supplied to the first reactor. However, improved results are obtained by injecting the catalyst fractionwise in several stages or in all stages. When initiating the reaction, the hexenes and the catalyst can be introduced into the reactor (s), propylene being supplied thereafter.

The invention is not limited to the use of specific dimerization catalysts of the above type, or to the use of determined proportions of these catalysts, or to the use of specific operating conditions. It is however essential to use a soluble catalyst and to operate in liquid phase in order to obtain favorable nonenes structures.

EXAMPLE 500 g/h of a hexenes mixture previously obtained by dimerization of propylene in the presence of a soluble dimerization catalyst consisting of nickel octanoate and dichloroethylaluminum are supplied to a reactor of a useful volume of 7 liters, provided with an external recirculation through a cooling exchanger.

The same catalyst as above is continuously introduced in an Al/Ni ratio of 15:1, at a feed rate corresponding to 4 milligram-atom of nickel per hour. 500 g/h of a $C_3$ cut formed of 94.5% propylene and 5.5% propane are introduced, while maintaining a temperature of 42° C. and a pressure of 20 bars. Under these conditions, the propylene concentration is 0.4% by weight. The reaction mixture is discharged at a rate of 1 kg/h and fractionated. The propane-propylene fraction (32.2 g/h, including 4.7 g/h of propylene) is removed, and the hexenes fraction (656.1 g/h) is partly recovered (156.1 g/h) and partly recycled to the reactor (500 g/h). 187.8 g/h of nonenes, 88.1 g/h of dodecenes and 35.8 g/h of olefins higher than dodecenes are also obtained.

The above values correspond to a stabilized run of the plant. These values correspond to a (nonenes/propylene) yield of 39.7% b.w. and to a [(nonenes+dodecenes)/propylene] yield of 58.4% b.w. The formation of hexenes and olefins higher than dodecenes is thus avoided.

The resultant nonenes have a structure which is more favorable to a subsequent oxidation reaction than the nonenes obtained in the presence of phosphoric acid.

The most favorable structures, as concerns oxonation, are the mono- and disubstituted structures (first type); $-CH=CH_2$; $-CH=CH-$ and $CH_2=C<$.

The least favorable structures are the tri- and tetrasubstituted structures (second type); $-CH=C<$ and $>C=C<$.

In the above example, there has been obtained 44.5% of structures of the first type, 7.5% of which are monosubstituted (with phosphoric acid, the proportion is 21.8% of structures of the first type, with 0% monosubstituted), and 55.5% of structures of the second type (with phosphoric acid: 78.2%).

COMPARISON EXAMPLE

In this example, the operation is conducted without recycling hexenes. 1000 g/h of the same $C_3$ cut is introduced in that case and the effluent is fractionated, 58.8 g/h of the propane-propylene cut containing 3.8 g/h of propylene, 383.1 g/h hexenes, 271 g/h of nonenes, 177 g/h of dodecenes and 110 g/h of olefins higher than dodecenes are thus obtained.

The (nonenes/propylene) yield is only 28.7% b.w. and the [(nonenes+dodecenes)/propylene] yield 47.4% b.w., the proportion of by-products being greater than in the example according to the invention.

What is claimed is:

1. A process for producing nonenes or a mixture of nonenes and dodecenes, comprising the steps of: introducing propylene into a liquid reaction phase comprising hexenes, in the presence of a soluble dimerization catalyst, at a temperature of 20°-60° C., the amount of propylene being controlled so as to maintain a propylene concentration in the liquid reaction phase of 0.05-1% by weight, withdrawing a portion of the liquid reaction phase, separating and recovering nonenes and higher olefins therefrom, and recycling at least a portion of the remaining withdrawn liquid phase of high hexenes content to the reaction zone.

2. A process according to claim 1, wherein the reaction temperature is 35°-50° C.

3. A process according to claim 1, wherein the reaction liquid phase is circulated loopwise successively through a reactor and a heat exchanger, with a residence time of the reaction mixture of from 1 to 12 hours.

4. A process according to claim 1, wherein the soluble catalyst consists of the reaction product of a nickel compound with an aluminum compound.

5. A process according to claim 4, wherein the catalyst is obtained by admixing at least one nickel carboxylate with at least one dichloroalkylaluminum.

6. A process according to claim 1 wherein the catalyst is used in a proportion of 0.1 to 20 milligram-atom of nickel per kilogram of the propylene feed charge.

* * * * *